United States Patent [19]
Anthony

[11] Patent Number: 5,541,972
[45] Date of Patent: Jul. 30, 1996

[54] DISPOSABLE PADDING DEVICE FOR A MAMMOGRAPHY X-RAY PLATE

[76] Inventor: Betty J. Anthony, 6480 Milton St., Philadelphia, Pa. 19119

[21] Appl. No.: 51,389

[22] Filed: Apr. 23, 1993

[51] Int. Cl.⁶ ........................................ A61B 6/04
[52] U.S. Cl. ............................. 378/37; 378/208
[58] Field of Search ........................................ 378/37

[56] References Cited

U.S. PATENT DOCUMENTS

| | | | |
|---|---|---|---|
| 1,631,497 | 6/1927 | Marler | 378/169 |
| 4,117,782 | 10/1978 | Cahill | 108/27 |
| 4,703,531 | 11/1987 | Bissett | 5/508 |
| 4,710,992 | 12/1987 | Falwell et al. | 5/508 |
| 5,044,008 | 8/1991 | Jackson | 378/168 |

*Primary Examiner*—Craig E. Church

[57] ABSTRACT

A padding device for a mammography system that can be removably attached to the face surface of the X-ray plate used within the mammography system. The padding device covers the face surface of the X-ray plate, thereby providing a clean sterile surface for contact with the patient's body. Furthermore, the padding device positions padding material over the top edge and the side surfaces of the face surface, thereby providing cushioning between those points and a patient's body. The presence of cushioning at these points greatly reduces the amount of discomfort experienced by a patient during a mammography.

14 Claims, 12 Drawing Sheets

DISPOSABLE PADDING DEVICE FOR A MAMMOGRAPHY X-RAY PLATE

BACKGROUND OF THE INVENTION

1. Field of the Invention

The present invention relates to a sterile, disposable padding device that can be positioned on the edge of an X-ray plate in a mammography system. More particularly, the present invention relates to a padding device that reduces the discomfort experienced by a patient as the patient's body is pressed against the hard edges of an X-ray plate during a mammographic examination.

2. Prior Art Statement

A mammographic examination, commonly called a mammography, is when X-ray images are obtained of a patient's breast tissues and the surrounding muscles. By viewing X-ray images obtained during a mammography, abnormalities such as malignancies and cysts can be detected long before they can be detected in a conventional tactile examination. Consequently, mammographies have become an essential tool in providing early detection of breast cancer and other diseases that effect the tissues of the breast. Early detection in breast cancer and like ailments is essential in effectively treating and curing the disease. As such, the development of mammography systems in medicine and the increasing number of patients who receive regular mammographic examinations has resulted in the early detections of many cases of breast cancer and has greatly increased the cure rate for treating breast cancer.

Mammography has become such an important part of the early detection of diseases of the breast, that many doctors now recommend that women over the age of forty receive annual mammographies as part of their routine medical care. By receiving annual examinations, it is probable that if a woman does ever develop breast cancer or another disease of the breast, then the annual mammography will detect that disease at an early stage where the likelihood of successfully treating the disease is at its highest. A mammography is not an overly time consuming or expensive medical procedure, yet every year many women do not submit themselves to a mammographic examination. As a result, many cases of breast cancer and other diseases of the breast are going undetected. The longer the disease goes without detection, the less likely it is that the disease can be successfully treated. Consequently, by not having annual mammographies, many women are jeopardizing their health.

One of the primary reasons women choose not to receive a mammography is that the mammography causes a great deal of physical discomfort. In a mammography, X-ray images are taken of a patient's breast from different perspectives. In order to include as much breast tissue in each X-ray image, the patient is required to lean into the X-ray plate as the X-ray images are taken. As will be later explained, it is the force of the X-ray plate against various parts of the patient's body that causes a large part of the discomfort experienced.

Referring to FIG. 1, there is shown a conventional mammography system 10 such as is currently commercially manufactured by General Electric and sold under the model name SENOGRAPHE 6OOT SENIX H.F.. The mammography system 10 includes an X-ray source 12, an X-ray plate 14 and a compression plate 16 positioned between the X-ray plate 14 and X-ray source 12. As will be later explained, the compression plate 16 is movable between the X-ray source 12 and the X-ray plate 14 and is used to compress breast tissue against the X-ray plate 14 before the X-ray images are taken. The X-ray plate 14 has a top surface 18 on which a patient's breast tissue will eventually rest. An X-ray film cartridge 20 slides into an opening below the top surface 18. X-ray radiation emanates from the X-ray source 12, passes through the compression plate 16, the patient's breast tissue and the top surface 18 of the X-ray plate 14 to create the desired X-ray images on the X-ray film cartridge 20.

As a patient's breast tissue is placed on the X-ray plate 16, the patient's body contacts the face surface 22 of the X-ray plate 14. The face surface 22 is rigid, having top edge 24 that joins the face surface 22 to the top surface 18, and two corner edges 26, 27 that join the face surface 22 to the two side surfaces 28, 29 of the X-ray plate 14. Different parts of a patient's body contact the face surface 22, its top edge 24 and its two corner edges 26, 27 during the mammographic examination. As the sharp rigid shape of the top edge 24 and the corner edges 26, 27 press against the patient's body, great discomfort is caused to the patient. Additionally, as a patient's skin contacts the face surface 22 of the X-ray plate 14, the X-ray plate 14 cannot be kept sterile unless it is cleaned and disinfected after each use. Furthermore, the X-ray plate 14 is often cold, causing discomfort to the patient upon contact with the patient's body.

During a mammographic examination, X-ray images are obtained for a patient's breast tissue from a plurality of perspectives. Referring to FIG. 2, there is shown a patient 30 undergoing a mammography on the previously described mammography system 10 so as to obtain a cranicaudal projection of the patient's breast 31. To obtain a cranicaudal projection, the patient 30 must lean her body against the face surface 22 of the X-ray plate 14 so that her breast 31 extends as far as possible across the top surface 18 of the X-ray plate 14. The compression plate 16 then is used to compress the breast 31 against the compression plate 16 so as to flatten the breast 31. When positioned for a craniocaudal projection, the patient's ribs are pressed hard against the face surface 22 of the X-ray plate 14. Furthermore, one of the corner edges 26 of the X-ray plate 14 is pressed against the patient's sternum and the sharp top edge 24 of the X-ray plate 14 is pressed hard against the underside of the patient's breast 31. The contact of the X-ray plate 14 against the patient 30 at these positions causes great discomfort to the patient 30.

In FIG. 3, the patient 30 is shown positioned with the mammography system 10 so as to obtain a mediolateral oblique view of the patient's breast 31. In this orientation, one edge corner 27 of the X-ray plate 14 is placed under the patient's arm 33 where it is pressed into the patient's axilla and causes great discomfort. The opposite edge corner 26 of the X-ray plate is pressed against the patient's rib cage. Furthermore, the sharp top edge 24 of the X-ray plate 14 is pressed against the underside of the breast 31. The position of the X-ray plate 14 during the mediolateral oblique view is again extremely uncomfortable to the patient 30.

In FIG. 4, the patient 30 is shown positioned with the mammography system 10 so as to obtain a lateromedial projection of the patient's breast 31. In this orientation the X-ray plate 14 passes down the center of the patient's torso, wherein one corner edge 26 of the X-ray plate 14 presses against the neck of the patient, while the opposite end corner 27 presses against the patient's stomach. The top edge 24 of the X-ray plate 14 is pressed across the sternum, and depending upon the size of the patient 30, may cross the throat of the patient. The position of the X-ray plate 14 during lateromedial projection is again extremely uncomfortable to the patient 30.

It will be understood that in the practice of mammographic examinations, there are many different projected orientations that may be taken of a patient's breast. In each of these projected orientations, however, the patient is required to lean against the face surface of the X-ray plate. Consequently, the patient experiences discomfort as the hard edges and corners of the X-ray plate press into the patient's body. In view of the discomfort caused by mammography systems, there exists a need for a disposable padding device that can be placed over the edges of the X-ray plate before a patient is required to lean against the X-ray plate. As such, the hard corners and edges of the X-ray plate can be cushioned while providing a disposable sanitary surface.

The prior art is replete with devices that are used to cushion the edges of objects, however these devices cannot be applied to mammography systems without adversely effecting the operation of the mammography system. For example, in U.S. Pat. No. 4,710,992 to Falwell et al, a padding device is disclosed for use in padding the hard edges of a bed rail. The Falwell device uses metal spring clips to form a friction fit during installation. The spring clips are radiopaque, as such the Falwell device cannot be used on a mammography system because the spring clips would obstruct the X-ray beam used to create the X-ray images being collected.

In U.S. Pat. No. 4,703,531 to Bissett, a padding device is disclosed that is designed to cover a support beam for a bed. The padding device is typical of many prior art padding devices in that no importance is placed on the radiopaqueness of the design. The Bissett device utilizes thick padding, wooden blocks, metal clamps and metal staples in its construction. As a result, the Bissett device cannot be used to pad an X-ray plate because the Bissett device would block the impinging X-ray beam and cause useless X-ray images.

Another problem with many conventional prior art padding devices is that they are expensive to manufacture and difficult to install, therefore making such prior art padding devices impractical for use on a mammography system. For example, in U.S. Pat. No. 4,117,782 to Cahill, entitled GUARD FOR PREVENTING HUMAN INJURIES ON IMPACT WITH FURNISHINGS, a padding guard is described that is tied around the edges of a piece of furniture with a length of flexible strapping. In such an arrangement, the time and labor required in attaching and removing the padding from the edge of an object would preclude its use as an effective one-time-use, sterile and disposable device.

It is therefore an objective of the present invention to provide a padding device that can be attached to the hard edges of an X-ray plate in a mammography system, wherein the present invention padding device is sterile, disposable, easy to install and remove, inexpensive to manufacture and does not adversely effect the X-ray images being created during the mammography.

BRIEF DESCRIPTION OF THE DRAWINGS

For a better understanding of the present invention, reference is made to the following description of exemplary embodiments thereof, considered in conjunction with the accompanying drawings, in which.

SUMMARY OF THE INVENTION

The present invention is a padding device for use on an X-ray mammography machine. During a mammography, a patient is required to press her body against the face surface of an X-ray plate so as to position as much breast tissue as possible over the X-ray plate. The face surface of the X-ray plate, that contacts the patient's body, has a hard top edge as well as hard side edges and cause great discomfort to the patient. The present invention is a padding device that can be removably attached to the face surface of the X-ray plate. The padding device covers the face surface of the X-ray plate, thereby providing a clean sterile surface for contact with the patient's body. Furthermore, the padding device positions padding material over the top edge and the side surfaces of the face surface, thereby providing cushioning between those points and a patient's body. The presence of cushioning at these points greatly reduces the amount of discomfort experienced by a patient during a mammography.

In an X-ray mammography machine, X-ray images are obtained for breast tissue positioned over a predetermined area on the X-ray plate. The present invention padding device attaches to the X-ray plate so as to not interfere with the X-ray images being obtained. Furthermore, the thickness of the padding along the X-ray plate is distributed so as not to hold a patient away from the X-ray plate by any appreciable distance. Consequently, the present invention padding device removes the discomfort of a mammographic examination without appreciably detracting from the quality of the mammographic examination.

DETAILED DESCRIPTION OF THE INVENTION

Figure 1:
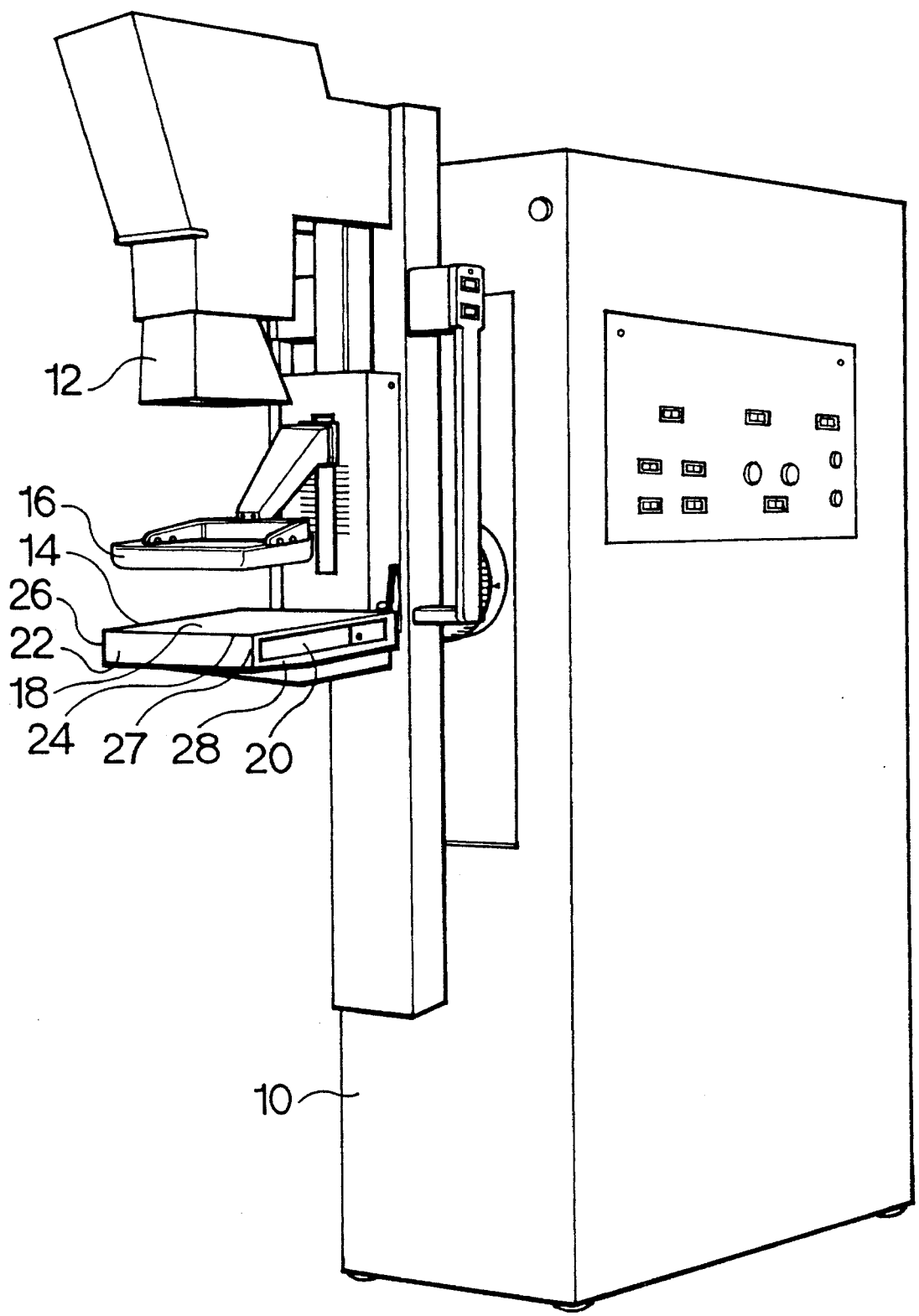
FIG. 1, is a perspective view of a prior art mammography X-ray machine.
Figure 2:
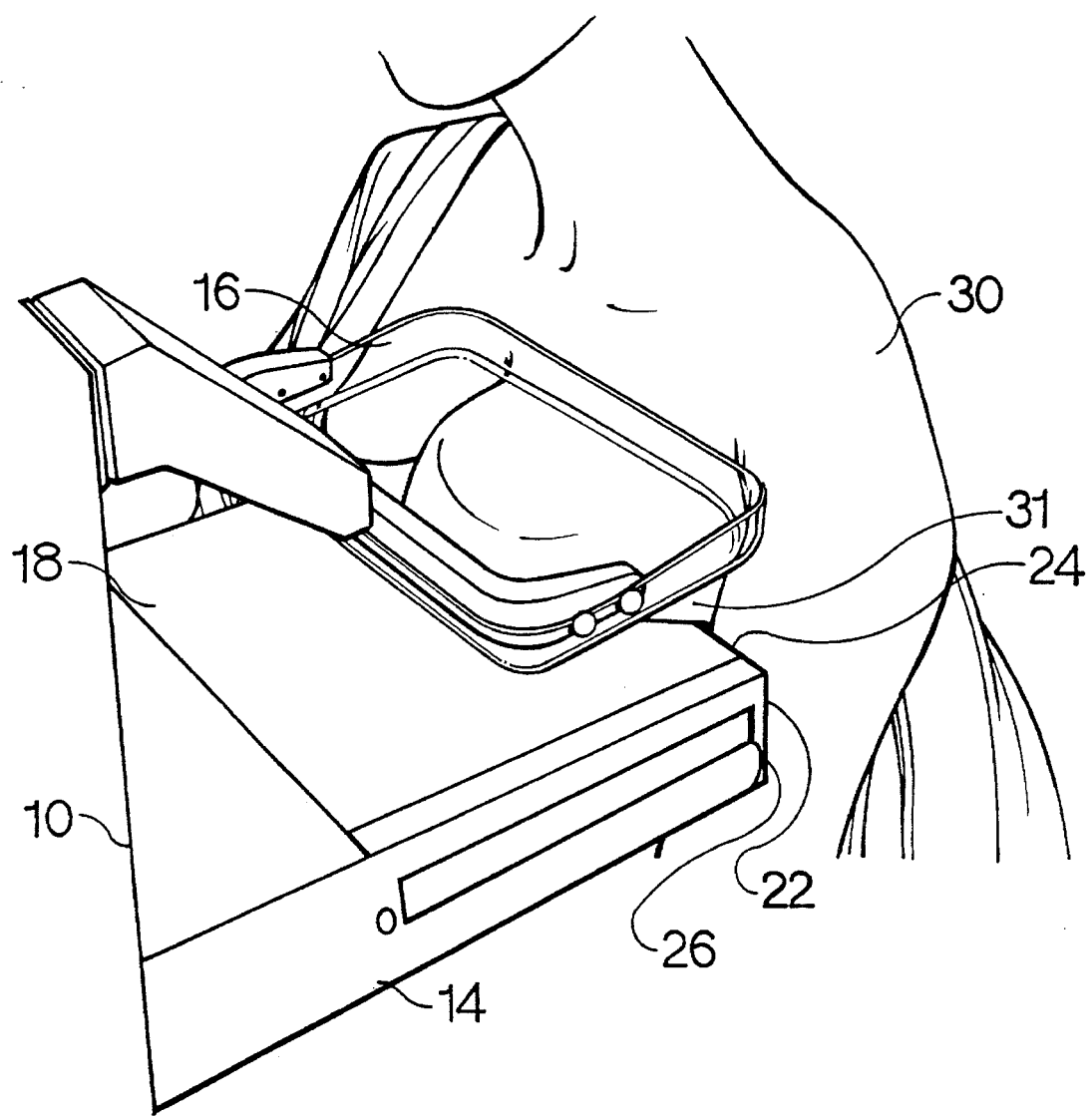
FIG. 2, shows a patient in conjunction with a mammography X-ray machine undergoing a craniocaudal projection.
Figure 3:
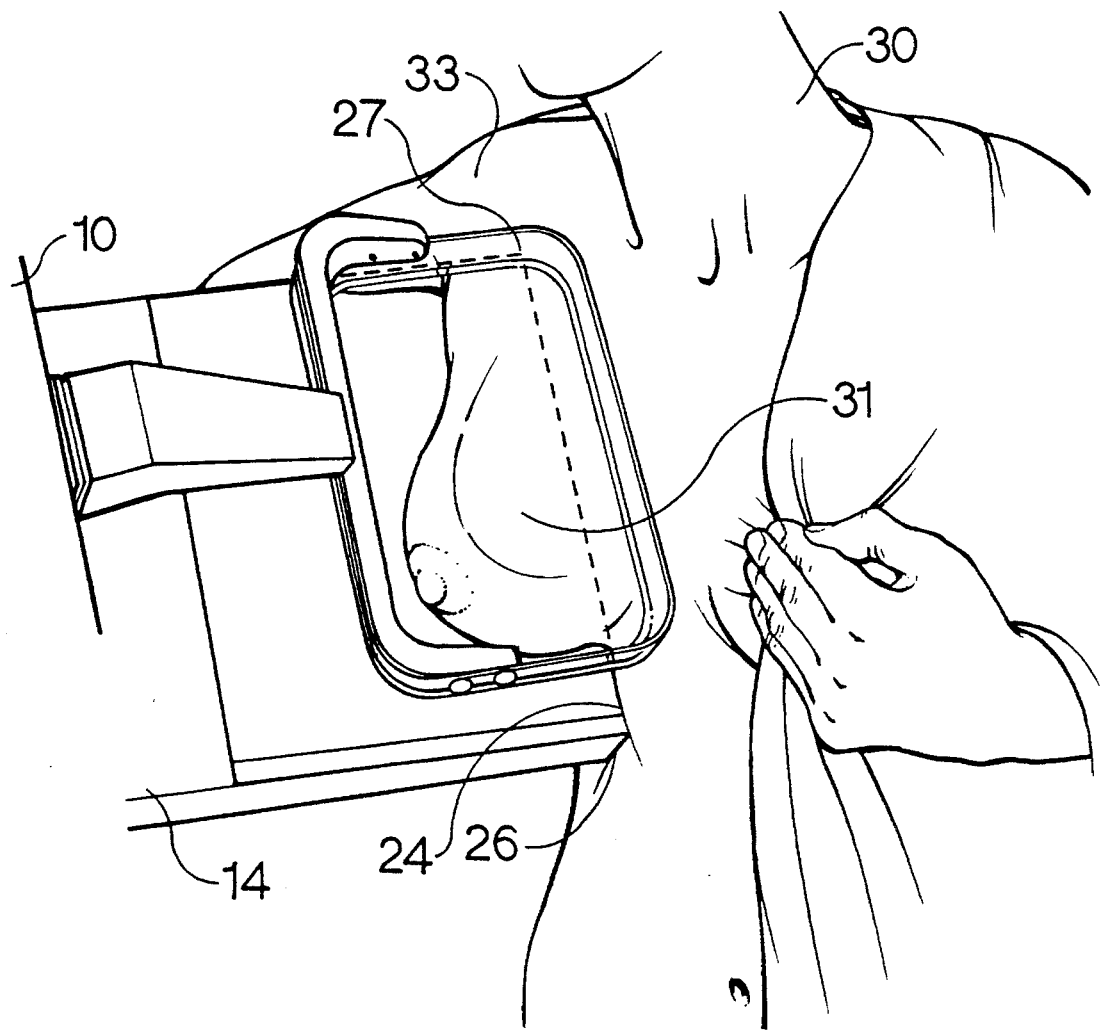
FIG. 3, shows a patient in conjunction with a mammography X-ray machine undergoing a mediolateral oblique projection.
Figure 4:
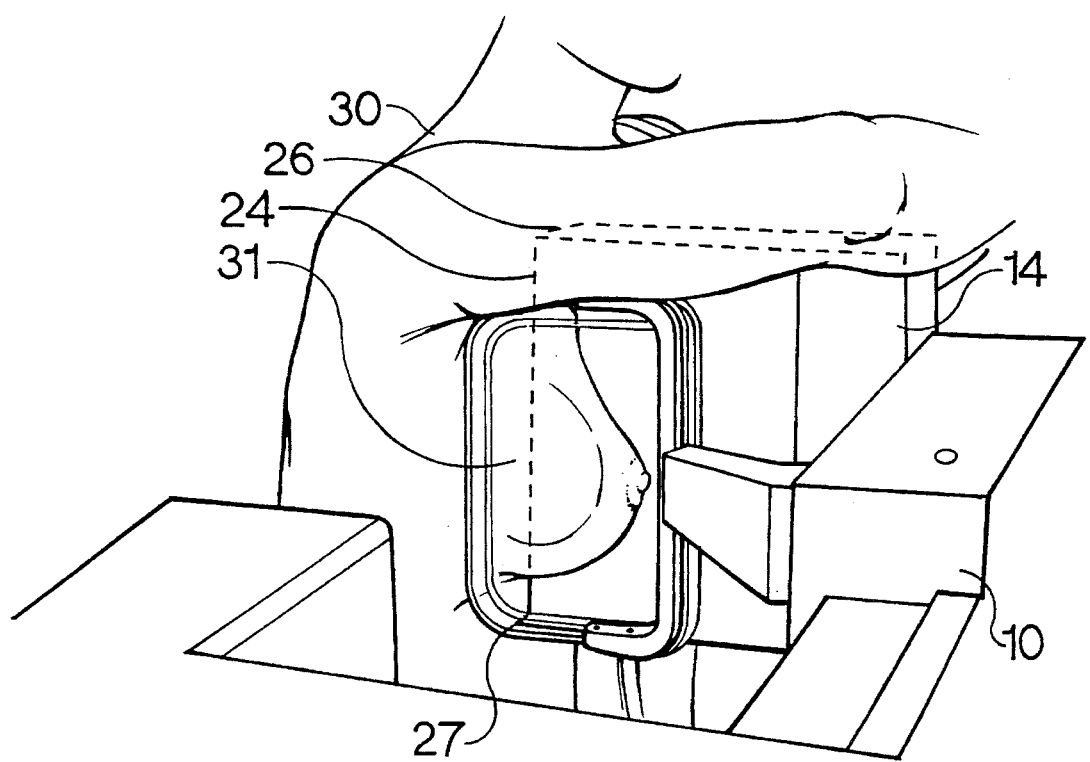
FIG. 4, shows a patient in conjunction with a mammography X-ray machine undergoing a lateromedial projection.
Figure 5:
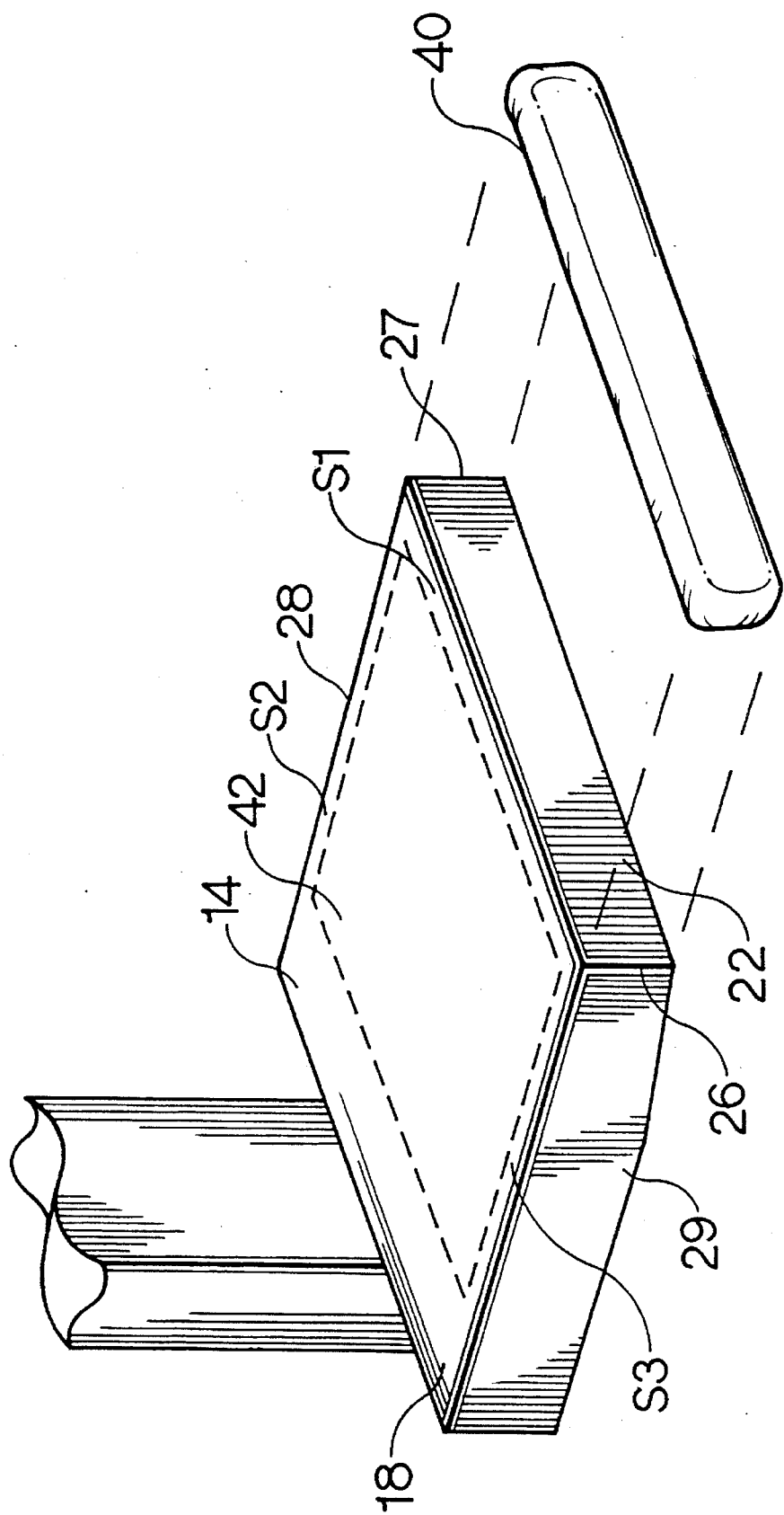
FIG. 5, is a perspective view of one preferred embodiment of the present invention, shown in conjunction with an X-ray plate to facilitate discussion and consideration.

Referring to FIG. 5, one preferred embodiment of the present invention padding device 40 is shown in conjunction with an X-ray plate 14 from a mammography system 10, as has been previously described in conjunction with FIGS. 1 through 4. The purpose of the present invention padding device 40 is to provide a sterile, disposable cover for the face surface 22 of the X-ray plate 14, and provide a padded surface across the corner edges 26, 27 and the top edge 24 of the X-ray plate 14. As will be explained, the padding provided will be positioned in such a manner so as not to interfere with any X-ray image being obtained during the mammography.

During a mammography, X-ray images are obtained for breast tissue that is placed on the top surface 18 of the X-ray plate 14. The size of the X-ray image that is obtained is dependent upon the size of the X-ray film cartridge placed below the X-ray plate 14. Despite the size of the X-ray film cartridge below the X-ray plate 14, the X-ray film cartridge is never as large as is the top surface 18 of the X-ray plate 14. In FIG. 5, the position of the X-ray film cartridge below the top surface 18 of the X-ray plate 14 is indicated as region 42. Looking toward region 42, it can be seen that there exists a small space S1 that exists between the film cartridge region 42 and the face surface 22 of the X-ray plate 14. Similarly, small spaces S2, S3 exist between the sides of the film cartridge region 42 and the side surfaces 28, 29 of the X-ray plate 14. It will therefore be understood that during a mammography, X-ray images are obtained only for breast tissue placed on the top surface 18 of the X-ray plate 14 that is placed over the film cartridge region 42. Any tissue that is not above the film cartridge region 42 is not imaged. It is for this reason that women are required to lean hard against the face surface 22 of the X-ray plate 14 during a mammography. By leaning hard against the X-ray plate 14, more breast tissue extends over the film cartridge region 42 of the X-ray plate 14.

Figure 6:
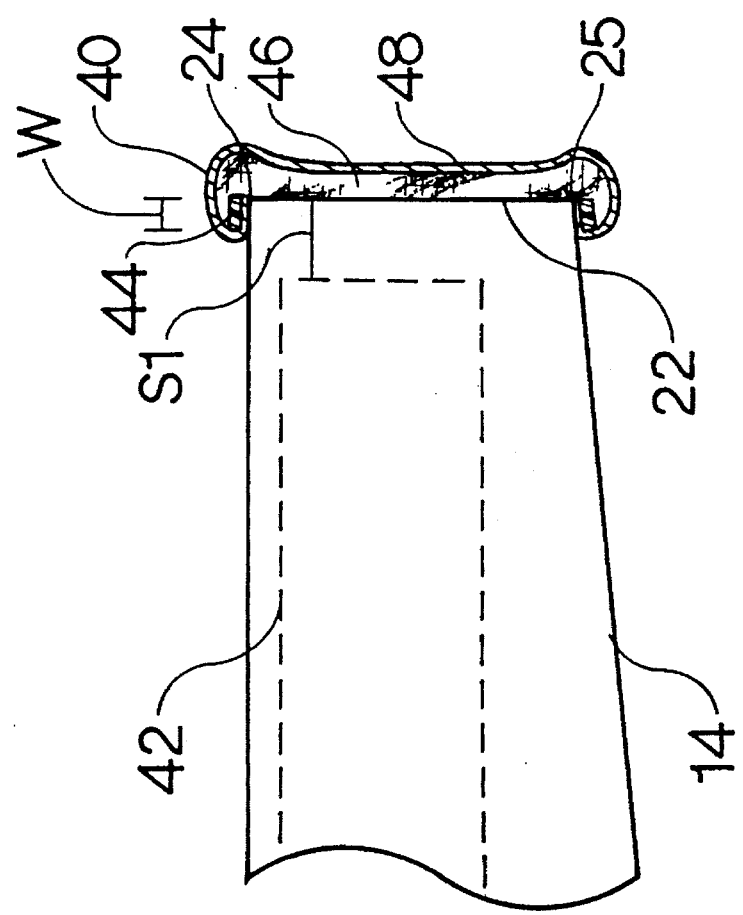
FIG. 6, is a cross-sectional view of the embodiment of FIG. 5, viewed along section line 6—6.
Figure 7:
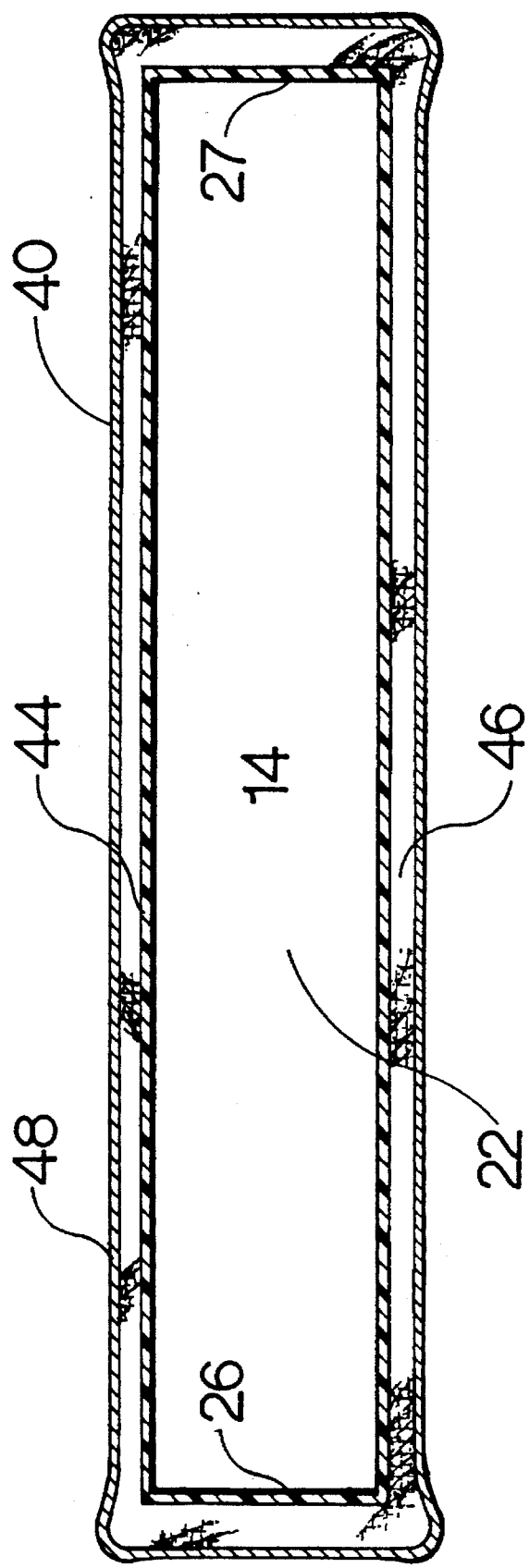
FIG. 7, is a cross-sectional view of the embodiment of FIG. 5, viewed along section line 7—7.

Referring to FIGS. 6 and 7 in conjunction with FIG. 5, it can be seen that the present invention padding device 40 is comprised of an elastic band 44, padding material 46 and an outer paper covering 48. The size of the elastic band 44 is smaller than the periphery of the face surface 22 of the X-ray plate 14. As such, the elastic band 44 must be stretched in order for the elastic band 44 to fit around the X-ray plate 14. The width W of the elastic band 44 is less than the space S1 that exists between the film cartridge region 42 and the face surface 22 of the X-ray plate 14. As a result, the elastic band 44 does not extend over the film cartridge region 42 when the elastic band 44 is placed around the periphery of the X-ray plate 14. Since the elastic band 44 does not extend above the film cartridge region 42, the elastic band 44 does not interfere with any X-ray image being obtained during the mammography.

The elastic band 44 is attached to padding. In the shown embodiment, the padding is comprised of a padding material 46 surrounded by a paper covering 48. The padding material 46 can be any known padding material such as cloth fibers, fluffed wood fibers, foam rubber or the like. The paper covering 48 is used to confine the padding material 46, but need not be present if the padding material 46 can maintain its own form. As can be seen from FIGS. 6 and 7, the distribution of the padding material 46 throughout the padding device 40, is not uniform. Rather, certain areas of the padding device 40 have much more padding material 46 than do others. In FIG. 6, it can be seen that the padding material 46 is more prevalent proximate the top edge 24 and the bottom edge 25 of the X-ray plate 14 than it is across the face surface 22 of the X-ray plate 14. The padding material 46 is minimized across the face surface 22 of the X-ray plate 14 so that the padding material 46 will not act to hold a patient's body away from the X-ray plate 14. As such, by minimizing the thickness of the padding material 46 over the face surface 22 of the X-ray plate 14, the present invention padding device 40 will not prevent a patient from being able to fully position a breast over the film cartridge region 42 of the X-ray plate 14. However, the presence of the padding material 46 proximate the face surface 22 of the X-ray plate 14 does provide a sterile, disposable surface across the face surface 22 and prevents a patient's body from pressing against the cold surface of the face surface 22.

The amount of padding material 46 is increased proximate the top edge 24 and the bottom edge 25 of the face surface 22. The increased padding at these points acts to cushion the hardness of these edges. Consequently, as a patient's body is pressed against the face surface 22 of the X-ray plate 14, the pain associated with the top edge 24 and the bottom edge 25 pressing into the patient's body is substantially reduced.

In FIG. 7, it can be seen that the amount of padding material 46 is highest proximate corner edges 26, 27 of the X-ray plate 14. The corner edges 26, 27 are the points on the face surface 22 that are most removed from the film cartridge region 42 (shown in FIG. 5). As such, The amount of padding material 46 at these positions can be relatively thick without having the padding material 46 interfere with any X-ray image obtained. It is the corner edges 26, 27 of the X-ray plate 14 that cause the most discomfort to a patient during a mediolateral oblique projection or a lateromedial projection. The increased padding material at these points acts to cushion the sharp edges and corners, thereby greatly decreasing the discomfort experienced by a patient.

The padding device 40 is applied to the X-ray plate 14 by stretching the elastic band 44 around the periphery of the X-ray plate 14, proximate the face surface 22 of the X-ray plate 14. As such, the padding device 40 can be quickly and easily applied to the X-ray plate 14. Similarly, the padding device 40 can be easily removed from the X-ray plate 14 and replaced so as to provide a sterile surface for each patient utilizing the mammography system.

Figure 8:
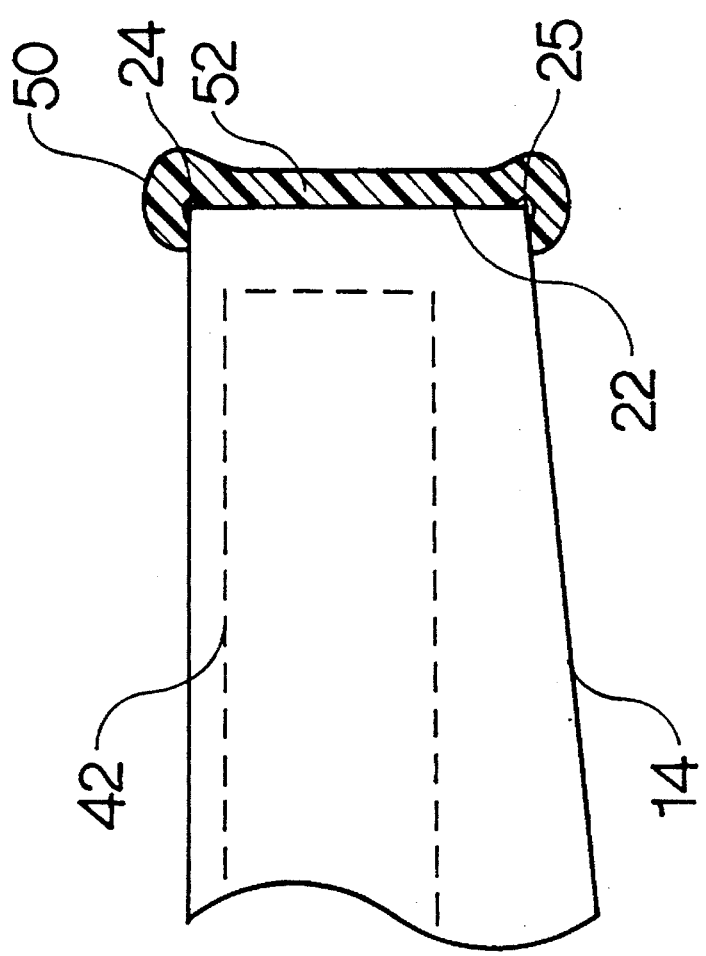
FIG. 8, is a cross-sectional view of a second embodiment of the present invention, viewed along the same section line as was FIG. 6.

Referring to FIG. 8, an alternative embodiment of a padding device 50 is shown in cross-section. In this embodiment, the entire padding device 50 is made of an elastomeric material 52. As such, an elastic band need not be present and the padding device 50 itself can be stretched and placed over the face surface 22 of the X-ray plate 14. The padding device 50 may have the same padding proportions as have been described in conjunction with the embodiment of FIGS. 6 and 7. As such, the elastomeric material 52 of the padding device 50 covers the face surface 22 of the X-ray plate 14 and provides padding to the top and bottom edges 24, 25, as well as the corner edges 26, 27 (shown in FIG. 5) of the X-ray plate 14. The elastomeric material 52 cushions these points, thereby decreasing the discomfort experienced by a patient as the patient presses against the X-ray plate 14. As the elastomeric material 52 is stretched over the X-ray plate 14, the elastomeric material does not extend over the film cartridge region 42. Consequently, the elastomeric material provides an easily installed, sterile and disposable cushioned surface without adversely effecting the X-ray images being obtained.

Figure 9:
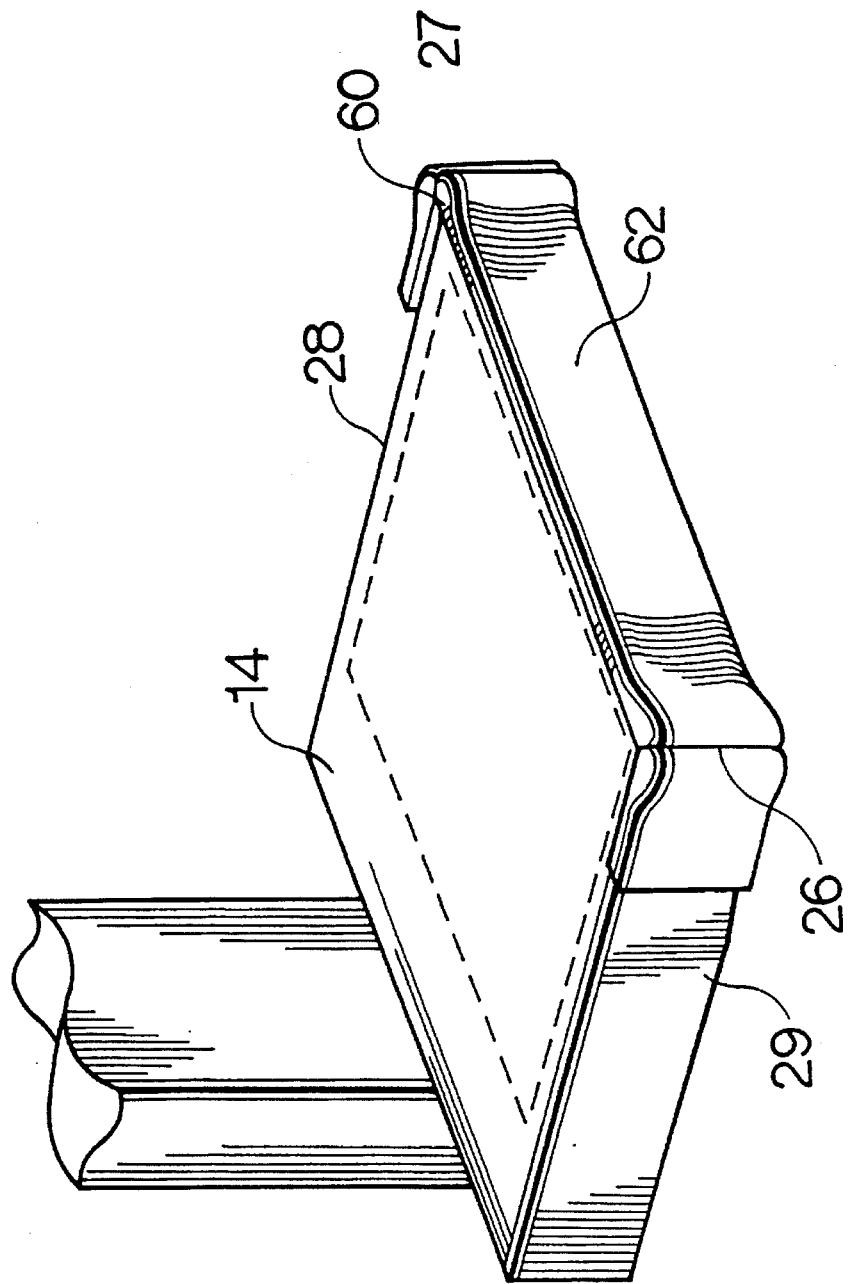
FIG. 9 is a perspective view of a third embodiment of the present invention, shown in conjunction with an X-ray plate to facilitate discussion and consideration.
Figure 10:
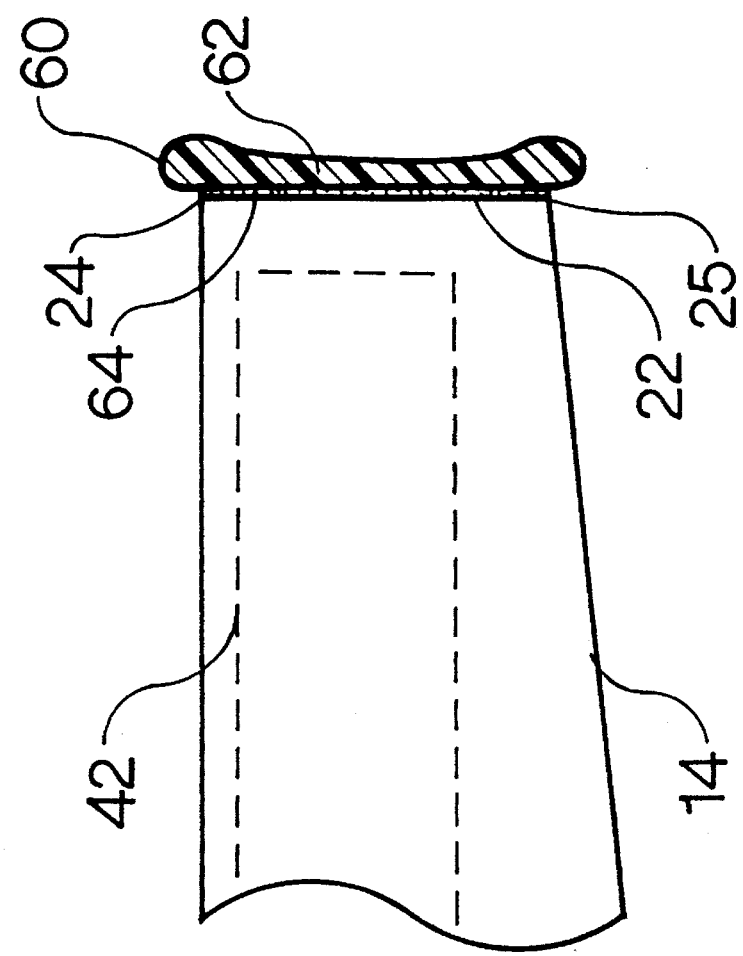
FIG. 10 is a cross-sectional view of the embodiment of FIG. 9, viewed along section line 10—10.

Referring to FIG. 9 in conjunction with FIG. 10, another alternate embodiment for the present invention padding device 60 is shown. In this embodiment, the padding device 60 is held onto the X-ray plate 14 with the use of a non-permanent adhesive. The padding device 60 shown is comprised of a strip of a padding material 62 placed over the face surface 22 of the X-ray plate 14 and curved around the two side surfaces 28, 29 of the X-ray plate 14. In FIG. 10, it can be seen that a film of adhesive 64 is disposed along one side of the padding material 62. The adhesive 64 may be originally covered with a removable backing that can be peeled away when the padding device 60 is applied to the X-ray plate 14. The adhesive 64 can be of any known type that provides a tacky surface yet does not create a permanent adhesion so that the padding device 60 can be peeled off the X-ray plate 14 when desired. The padding material 62 can be any known type of padding, such as fluffed wood fibers in a paper casing. However, in the shown embodiment, the padding material 62 is a molded piece of elastomeric material. The padding material 62 is thin as it passes over the face surface 22 of the X-ray plate 14. However, the thickness of the padding material 62 increases as it approaches the top and bottom edges 24, 25 of the X-ray plate 14. As has been previously explained, it is desirable to minimize the thickness of any padding over the face surface 22 of the X-ray plate 14, so as not to separate a patient from the X-ray plate 14. The padding material 62 extends slightly over the top edge 24 of the X-ray plate 14 and below the bottom edge 25 of the X-ray plate 14. As a patient's body presses against the X-ray plate 14, the padding material 62 deforms slightly over the top and bottom edges 24, 25 and acts to cushion the sharp points of both edge surfaces. As a result, the discomfort experienced by a patient is greatly reduced. As the padding material 62 deforms over the top edge 24 of the X-ray plate, the padding material does not extend across the film cartridge region 42. Consequently, the padding material does not interfere with the X-ray images being obtained.

In FIG. 9, it can be seen that the width of the padding material 62 increases as it approaches the corner edges 26, 27 of the X-ray plate 14. As such, the amount of padding proximate the corner edges 26, 27 of the X-ray plate 14 is greater than the center of the X-ray plate 14. The extra padding at these positions acts to alleviate the discomfort to a patient during a mediolateral oblique projection or a lateromedial projection.

Figure 11:
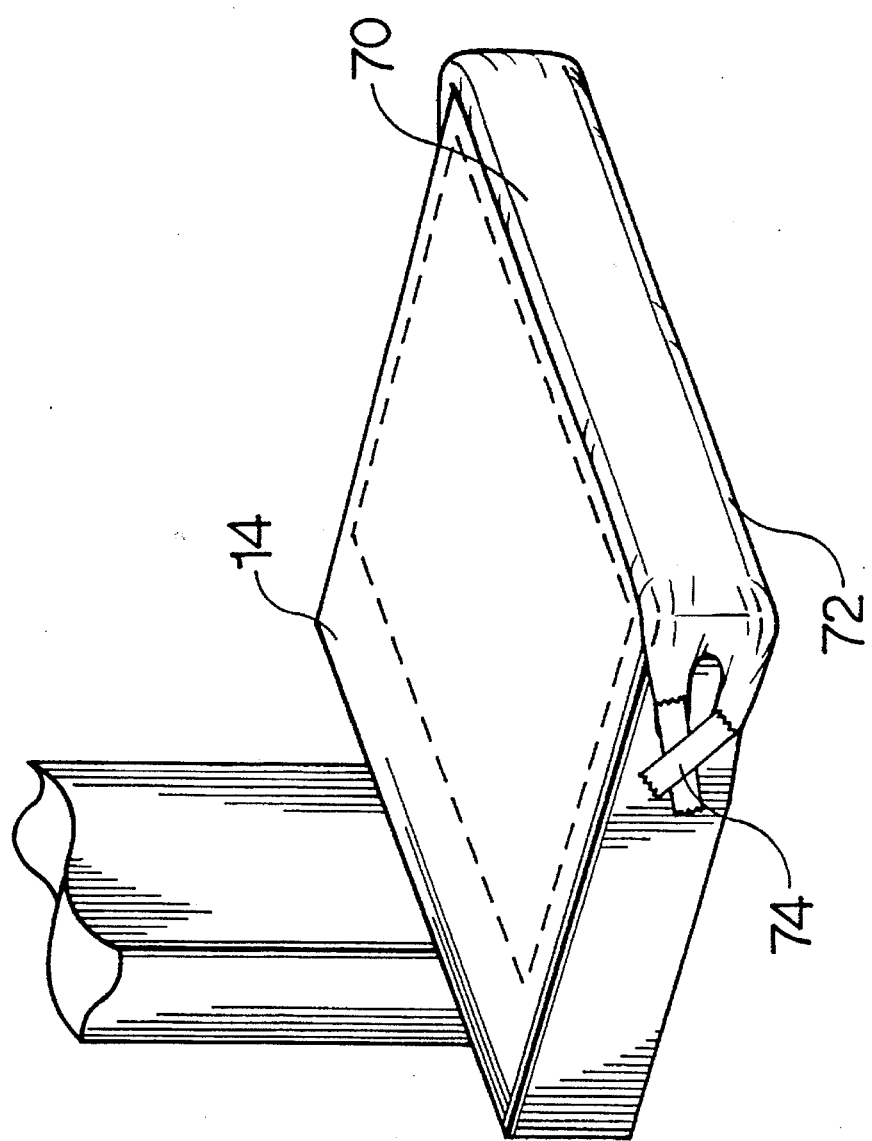
FIG. 11 is a perspective view of a fourth embodiment of the present invention, shown in conjunction with an X-ray plate.

Referring to FIG. 11, another embodiment of the present invention padding device 70 is shown, wherein the padding device is taped onto the X-ray plate 14. In this embodiment, the padding device 70 is comprised of padding material, such as fluffed wood fibers, held within a paper covering 72. Strips of tape 74 are attached to the ends of the padding device 70 so that the padding device 70 can be attached to the X-ray plate 14. The padding device 70 is shaped so as to cover the face surface of the X-ray plate and provide padding over the top and bottom edges of the X-ray plate, as well as over the corner edges of the X-ray plate. To remove the padding device 70 from the X-ray plate 14, the tape 74 is peeled away from the X-ray plate 14 and the padding device 70 is removed. The amount of padding contained within the padding device 70 is varied, as in previous embodiments, to provide extra cushioning in the regions of the edges and corners of the X-ray plate 14.

Figure 12:
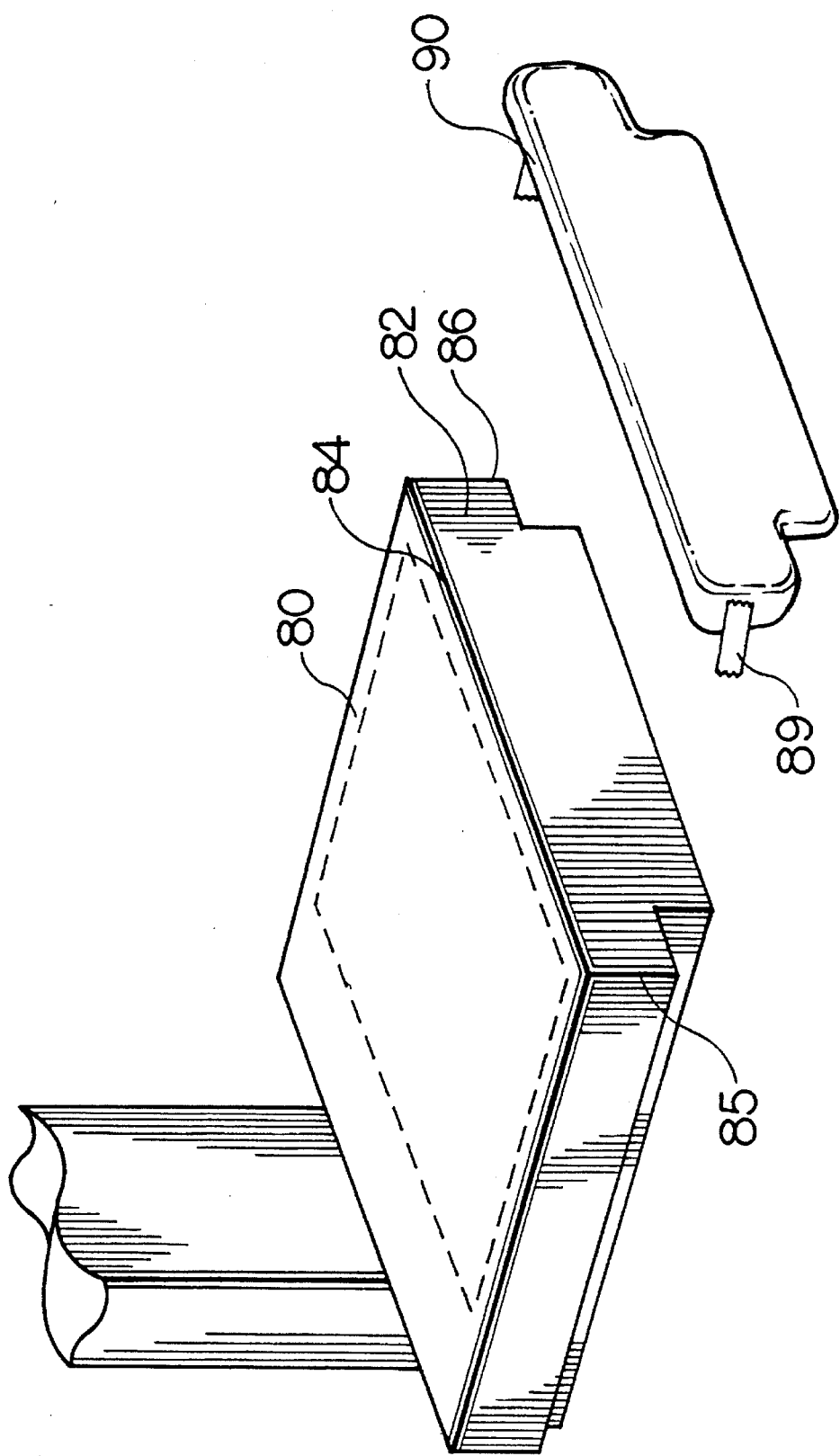
FIG. 12 is a perspective view of a fifth embodiment of the present invention, shown in conjunction with an X-ray plate having a complex face surface shape.

Referring to FIG. 12, there is shown an X-ray plate 80 that has a face surface 82 with a complex shape. With such an X-ray plate 80, it should be understood that only the top edge 84 of the X-ray plate 80 and the corner edges 85, 86 of the X-ray plate 80 contact a patient. As a result, it is only these surfaces that should be padded. However, in order to prevent discomfort from the usually cold temperature of the X-ray plate 80 and to assure sanitary conditions, it is desirable to cover any surface that may contact the patient's body during the mammographic examination. In FIG. 12, a padding device 90 is shown that is shaped to cover the entire face surface 82 of the X-ray plate 80, yet provides padding to the top edge 84 of the X-ray plate 80 and the corner edges 85, 86 of the X-ray plate 80. In the shown embodiment, the padding device 90 is held onto the X-ray plate 80 with strips of adhesive 89, however any other conventional means of attachment can also be used. The padding device 90 has padding material concentrated in the area of the corner edges 85, 86 and along the top edge 84 as has been previously described in other embodiments.

In each embodiment described, the padding added to the X-ray plate was added in a manner that would not interfere with the X-ray images being obtained during the mammographic examination. Additionally, the padding present in each embodiment was positioned to cushion the sharp edges and points that cause so many people discomfort during a mammography. It will be understood that in view of the plurality of embodiments described above, that features of some embodiments can be combined to form additional embodiments not specifically described. All such combinations are intended to be covered by the scope of this invention. Furthermore, the embodiments specifically described are merely exemplary and it should be understood that variations in materials, dimensions and functionally equivalent components can be made without departing from the spirit and scope of the invention as defined by the appended claims.

What is claimed is:

1. In a mammography system, wherein a patient's body is required to press against a face surface of an X-ray plate and wherein said face surface is defined between a top edge, bottom edge and two side edges, a disposable padding device for padding said face surface, comprising:

a paper cover sized to cover said face surface, thereby providing a sanitary barrier between the X-ray plate and the patient's body;

padding material affixed to said paper cover at positions corresponding to the positions of the top edge and two side edges of the X-ray plate;

attachment means for releasably attaching said paper cover and said padding material to said X-ray plate, wherein said padding material abuts against the top edge and the two side edges of the X-ray plate, thereby cushioning the top edge and the two side edges against the patient's body.

2. The padding device according to claim 1, wherein said mammography system creates X-ray images of a portion of said patient's body extending over a predetermined region of said X-ray plate and said attachment means attaches said paper cover and said padding material to said X-ray plate without said padding material extending over said predetermined region of said X-ray plate.

3. The padding device according to claim 2, wherein said padding material covers said bottom edge of said X-ray plate when said paper cover and said padding material are attached to said X-ray plate by said attachment means.

4. The padding device according to claim 2, wherein said padding material is affixed to said paper cover so that said padding material covers all of said face surface of said X-ray plate, when said padding material and said paper cover are attached to said X-ray plate by said attachment means, thereby cushioning all of the face surface from the patient's body.

5. The padding device according to claim 2, wherein said padding material is elastomeric and has a natural elasticity, whereby said padding material can be stretched over said face surface of said X-ray plate and is retained on said face surface by the natural elasticity of said padding material.

6. The padding device according to claim 2, further including an elastomeric member coupled to said paper cover, said elastomeric member being positionable around said X-ray plate proximate said face surface, whereby said elastomeric member holds said paper cover and said padding material over said face surface of said X-ray plate.

7. The padding device according to claim 2, wherein said attachment means includes an adhesive disposed on said padding material, whereby said padding material can be selectively joined to said X-ray plate by bringing said adhesive in contact with said X-ray plate.

8. The padding device according to claim 2, wherein said attachment means includes at least one piece of tape coupled to said paper cover, whereby said tape can be selectively applied to said X-ray plate thereby retaining said paper cover and said padding material on said X-ray plate.

9. The padding device according to claim 4, wherein said padding material is thicker at positions that contact said two side edges of said face surface then at positions that contact a central region of said face surface.

10. The padding device according to claim 9, wherein, when said padding material is attached to said X-ray plate, said padding material is thicker proximate said top edge of said face surface than is present over said central region of said face surface.

11. A method of reducing the discomfort experienced by a patient during a mammography created by the patient's body pressing against a face surface of an X-ray plate, wherein the face surface includes a top edge, bottom edge and two side edges, said method comprising the steps of:

providing a disposable paper cover sized to cover said face surface, thereby providing a sanitary barrier between the X-ray plate and the patient's body, wherein padding material is affixed to said paper cover at positions corresponding to the positions of the top edge and two side edges of the X-ray plate;

removably attaching said paper cover and said padding material to said X-ray plate wherein said padding material abuts against said top edge and said two side edges thereby cushioning said top edge and said two side edges against said patient's body.

12. The method according to claim 11, wherein said padding material covers all of said face surface, thereby cushioning said patient's body against said face surface.

13. The method according to claim 11, wherein said padding material is attached to said X-ray plate in a manner that does not permit said padding material from interfering with an X-ray image created during said mammography.

14. The method according to claim 13, further including the step of providing more padding over said top edge and said two side edges of said face surface than over the remainder of said face surface.

* * * * *